United States Patent
Ritzi

(10) Patent No.: US 7,147,860 B2
(45) Date of Patent: Dec. 12, 2006

(54) COMPOSITION FOR SYMPTOMATIC RELIEF OF VAGINITIS

(75) Inventor: Syed Ritzi, Bakersfield, CA (US)

(73) Assignee: Centum Research, LLC, Bakersfield, CA (US)

( * ) Notice: Subject to any disclaimer, the term of this patent is extended or adjusted under 35 U.S.C. 154(b) by 252 days.

(21) Appl. No.: 10/065,898

(22) Filed: Nov. 27, 2002

(65) Prior Publication Data

US 2003/0099716 A1    May 29, 2003

Related U.S. Application Data

(60) Provisional application No. 60/334,028, filed on Nov. 28, 2001.

(51) Int. Cl.
*A01N 65/00* (2006.01)
*A01N 59/06* (2006.01)

(52) U.S. Cl. ............ 424/195.15; 424/195.16; 424/400; 424/401; 424/402; 424/403; 424/404; 424/195.17; 424/195.18; 424/725; 424/780; 424/602; 424/538

(58) Field of Classification Search ........... 424/195.15, 424/195.16, 400, 401–404, 195.17, 195.18, 424/725, 780, 602, 538
See application file for complete search history.

(56) References Cited

U.S. PATENT DOCUMENTS

| | | | |
|---|---|---|---|
| 3,686,412 A | 8/1972 | Fitzmaurice | 424/283 |
| 4,192,860 A | 3/1980 | Griffiths | 424/43 |
| 4,271,182 A | 6/1981 | Sullivan | 424/283 |
| 5,098,709 A * | 3/1992 | Kang | 424/725.1 |
| 5,141,803 A * | 8/1992 | Pregozen | 442/123 |
| 5,532,270 A | 7/1996 | Clemente | 514/456 |
| 5,536,743 A | 7/1996 | Borgman | 514/398 |
| 5,618,550 A | 4/1997 | Ratcliff | 424/422 |
| 5,667,817 A | 9/1997 | Kross | 424/661 |
| 5,741,525 A | 4/1998 | Larsen | 424/616 |
| 6,027,716 A * | 2/2000 | Levin et al. | 424/58 |

\* cited by examiner

*Primary Examiner*—Sreeni Padmanabhan
*Assistant Examiner*—Shahnam Sharareh
(74) *Attorney, Agent, or Firm*—Jeffrey Furr

(57) ABSTRACT

Present invention relates to a method and composition for symptomatic relief of vaginitis. Until the treatment of underlying cause takes effect women suffer from unpleasant symptoms of vaginitis restricting daily routine activities. The symptoms of vaginitis may be incapacitating and are a common reason for visiting the gynecologist and can lead to frustration, embarrassment, anger, lost days from work, marital conflict and loss of ability to enjoy a normal personal, professional and social life.

16 Claims, 1 Drawing Sheet

Apis Mellifica, Borax, Hydrastis Canadensis, Kali Bichromicum, Helonias Dioica, Lycopodium Clavatum, Sepia, Agaricus Muscarius, Anagallis Arvensis, Dolichos Pruriens, Muriaticum Acidum, Oleander, Arsenicum Album, Kali Muriaticum, Berberis Vulgaris, Urtica Urens, Ignatia Amara, Pulsatilla and Cantharis. All in 30x potency.
Mineral oil 12% by weight
Avena Sativa 80% by weight
Calcium Silicate 7.37% by weight
Ethoxylated Aliphatic Alcohol 0.63% by weight Apis Mellifica, Borax, Hydrastis Canadensis, Kali Bichromicum, Helonias Dioica, Lycopodium Clavatum, Sepia, Agaricus Muscarius, Anagallis Arvensis, Dolichos Pruriens, Muriaticum Acidum, Oleander, Arsenicum Album, Kali Muriaticum, Berberis Vulgaris, Urtica Urens, Ignatia Amara, Pulsatilla and Cantharis. All in 30x potency.
Mineral oil 12% by weight
Avena Sativa 80% by weight
Calcium Silicate 7.37% by weight
Ethoxylated Aliphatic Alcohol 0.63% by weight

Figure 1

COMPOSITION FOR SYMPTOMATIC RELIEF OF VAGINITIS

CROSS REFERENCE TO RELATED APPLICATIONS

This is the non-provisional of provisional patent No. 60/334,028 filed Nov. 28, 2001.

BACKGROUND OF INVENTION

TECHNICAL FIELD

This invention relates generally to the treatment of vaginitis and related conditions of the lower genital tract in females.

1. Background Vaginitis refers to the inflammation of vagina most commonly caused by the infections described herein. Itching, burning, irritation, redness, soreness, discomfort and discharge are the common symptoms of vaginitis. Cure of vaginitis requires the treatment of the underlying cause. Until the treatment of underlying cause takes effect, which may take several days, women suffer from tormenting symptoms of vaginitis. This composition provides relief from the symptoms of vaginitis while patients are waiting for the underlying cause to be diagnosed and treated or until the treatment of the underlying cause becomes effective. The symptoms of vaginitis can be devastating for women to the point that they are not able to perform routine daily.

This composition provides fast, symptomatic relief from vaginitis and at the same time cleans the feminine area aiding in the healing process. It is natural and is free of local anesthetics. Use of this composition is as easy as taking a bath. Patients find taking bath soothing and cleansing. This treatment appeals to women who want an all natural solution to their problem and wish to avoid the need for messy creams with chemical ingredients. Women prefer this type of method over the creams that contain local anesthetics and require rubbing the feminine area with hands. Women find that creams and suppositories are messy. Women do not like numb fingers or messy undergarments from creams and suppositories.

The most common vaginal infections causing vaginitis are Chlamydia, Gonorrhea, bacterial vaginosis, trichomoniasis, and vaginal yeast infection or candidiasis. Some vaginal infections are transmitted through sexual contact, but others such as yeast infections probably are not. There may be other causes of vaginitis as well.

Bacterial Vaginosis Bacterial vaginosis (BV) is the most common cause of vaginitis symptoms among women of childbearing age. Previously called nonspecific vaginitis or Gardnerella-associated vaginitis, BV is associated with sexual activity. BV reflects a change in the vaginal ecosystem. This imbalance, including pH changes, occurs when different types of bacteria outnumber the normal ones. Instead of Lactobacillus bacteria being the most numerous, increased numbers of organisms such as Gardnerella vaginalis, Bacteroides, Mobiluncus, and Mycoplasma hominis are found in the vaginas of women with BV. A change in sexual partners and douching may increase the risk of acquiring bacterial vaginosis. Bacterial vaginosis is associated with Pelvic Inflammatory Disease and complications of pregnancy such as premature labor.

The primary symptom of BV is an abnormal, odorous vaginal discharge, itching and discomfort. The fish-like odor is noticeable especially after intercourse. A physician may observe these signs during a physical examination and may confirm the diagnosis by doing tests of vaginal fluid.

The test includes examining the sample of vaginal fluid under a microscope to detect the presence of the organisms associated with BV. Diagnosis is based on the absence of lactobacilli, the presence of numerous "clue cells" (cells from the vaginal lining that are coated with BV organisms), a fishy odor, and decreased acidity or change in pH of vaginal fluid. Treatment is antibiotics such as metronidazole or clindamycin.

Trichomoniasis Trichomoniasis is a common STD that affects 2 to 3 million Americans yearly. It is caused by a single-celled protozoan parasite called Trichomonas vaginalis.

In women symptoms usually appear within four to 20 days of exposure. These symptoms include a heavy, yellow-green or gray vaginal discharge, odor itching and discomfort during intercourse. Diagnosis includes examination of discharge under the microscope and visualization of Tichomonas vaginalis or the laboratory tests such as cultures. Trichomoniasis can be associated with other sexually transmitted diseases or the complications of pregnancy. Trichomoniasis is treated by Metronidazole Vaginal Yeast Infection Vaginal yeast infection or vulvovaginal candidiasis is a common cause of vaginitis. Approximately 75 percent of all women will experience at least one symptomatic yeast infection during their lifetimes. Yeast are always present in the vagina in small numbers, and symptoms only appear with overgrowth. Several factors are associated with increased symptomatic infection in women, including pregnancy, uncontrolled diabetes mellitus, and the use of oral contraceptives or antibiotics. Other factors that may increase the incidence of yeast infection include using douches, perfumed feminine hygiene sprays, and topical antimicrobial agents, and wearing tight, poorly ventilated clothing and underwear. Whether or not yeast can be transmitted sexually is unknown.

The symptoms of yeast infection in women may include discharge, odor, itching, and discomfort. The thick, whitish-gray discharge is typically described as cottage-cheese-like in nature, although it can vary from watery to thick in consistency. Most male partners of women with yeast infection do not experience any symptoms of the infection. A transient self-limiting rash and burning sensation of the penis, however, have been reported after intercourse if condoms were not used.

Diagnosis is based upon microscopic examination of vaginal secretions for evidence of yeast forms. Various antifungal vaginal/oral medications (butoconazole, miconazole, clotrimazole, tioconazole and fluconazole) are available to treat yeast infection.

Chlamydia

This infection is a common bacterial sexually transmitted disease, with an estimated 4 to 8 million new cases occurring each year. Chlamydial infection may cause an abnormal genital discharge, discomfort and burning with urination. In women, untreated chlamydial infection may lead to pelvic inflammatory disease, one of the most common causes of ectopic pregnancy and infertility in women. Cultures are used for the diagnisis of Chlamydia and the treatment includes antibiotics like Tetracycline.

Gonorrhea

The symptoms of gonorrhea are a discharge from the vagina often with an odor, discomfort, soreness and painful or difficult urination. The most common and serious complications occur in women and, as with chlamydial infection; these complications include pelvic inflammatory disease (PID), ectopic pregnancy, and infertility. Cultures are used for diagnosis and antibiotics for the treatment.

SUMMARY OF INVENTION

The present invention relates to the treatment of vaginitis and related conditions of the lower genital tract in females.

Accordingly, it is an object of the present invention to provide a symptomatic treatment of vaginitis.

Another objective is to provide a symptomatic treatment of sexually transmitted diseases as well as the treatment of vaginal dryness, burning sensations around the vagina, of vaginal irritation, of redness around the vagina, of vaginal discomfort, of vaginal soreness, of vaginal redness.

Further objective is to provide a method of removing the dead tissue from the vagina, a method of cleansing the vagina and vaginal area during inflammation and a method of cleansing the vagina and vaginal area during infections.

The composition is: Apis Mellifica, Borax, Hydrastis Canadensis, Kali Bichromicum, Helonias Dioica, Lycopodium Clavatum, Sepia, Agaricus Muscarius, Anagallis Arvensis, Dolichos Pruriens, Muriaticum Acidum, Oleander, Arsenicum Album, Kali Muriaticum, Berberis Vulgaris, Urtica Urens, Ignatia Amara, Pulsatilla and Cantharis. All in 30× potency.

Mineral oil 12% by weightAvena Sativa 80% by weightcalcium Silicate7.37% by weightEthoxylated Aliphatic Alcohol 0.63% by weight.

BRIEF DESCRIPTION OF DRAWINGS

Without restricting the full scope of this invention, the preferred form of this invention is illustrated in the following drawings: FIG. 1 shows the ingredients.

DETAILED DESCRIPTION

This invention contains a unique combination of homeopathic and non homeopathic ingredients to provide symptomatic relief from vaginitis.

This composition provides fast, symptomatic relief from vaginitis and at the same time cleans the feminine area aiding in the healing process. It is natural and is free of local anesthetics. Use of this composition is as easy as taking a bath. Patients find taking bath soothing and cleansing. This treatment appeals to women who want an all natural solution to their problem and wish to avoid the need for messy creams with chemical ingredients. Women prefer this type of method over the creams that contain local anesthetics and require rubbing the feminine area with hands.

The composition as shown in FIG. 1 is comprised of: Apis Mellifica, Borax, Hydrastis Canadensis, Kali Bichromicum, Helonias Dioica, Lycopodium Clavatum, Sepia, Agaricus Muscarius, Anagallis Arvensis, Dolichos Pruriens, Muriaticum Acidum, Oleander, Arsenicum Album, Kali Muriaticum, Berberis Vulgaris, Urtica Urens, Ignatia Amara, Pulsatilla and Cantharis. All in 30× potency.

Mineral oil 12% by weight Avena Sativa 80% by weight Calcium Silicate 7.37% by weight Ethoxylated Aliphatic Alcohol 0.63% by weight. This composition is comprised of botanical and non-botanical ingredients.

This can be repeated as needed. Using the bath is a submersion method of applying the composition.

The composition can also be mixed with warm water and applied to the vagina and the area affected by vaginitis through any standard application method for applying such a solution to the vagina and the area affected by vaginitis. Such methods are well known in the art.

The composition is used for the symptomatic treatment of vaginitis. It can also be used as a symptomatic treatment of sexually transmitted diseases as well as the treatment of vaginal dryness, burning sensations around the vagina, of vaginal irritation, of redness around the vagina, of vaginal discomfort, of vaginal soreness, of vaginal redness. It can also be used as a method of removing the dead tissue from the vagina, a method of cleansing the vagina and vaginal area during inflammation and a method of cleansing the vagina and vaginal area during infections.

Alternative Embodiments:

As an alternative embodiment, the composition can be made where Mineral Oil comprises approximately 10–20% of the said composition.

As an alternative embodiment, the composition can be made where Avena Sativa comprises approximately 60–90% of the said composition.

As an alternative embodiment, the composition can be made where Calcium Silicate comprises approximately 5–10%.

As an alternative embodiment, the composition can be made where Ethoxylated Aliphatic Alcohol comprises approximately 0.5–5%.

The foregoing is considered as illustrative only of the principles of the invention. Further, since numerous modifications and changes will readily occur to those skilled in the art, it is not desired to limit the invention to the exact composition and methods described, and accordingly, all suitable modifications and equivalents may be resorted to, falling within the scope of the invention.

It is to be understood that the foregoing description is exemplary and explanatory but are not restrictive of the invention.

The invention claimed is:

1. A Composition suitable for the treatment of vaginitis which comprises: Borax in 30× potency, Kali Bichromicum in 30× potency, Helonias Dioica in 30× potency, Lycopodium Clavatum in 30× potency, Sepia in 30× potency, Agaricus Muscarius in 30× potency, Anagallis Arvensis in 30× potency, Dolichos Pruriens in 30× potency, Muriaticum Acidum in 30× potency, Oleander in 30× potency, Arsenicum Album in 30× potency, Kali Muriaticum in 30× potency, Berberis Vulgaris in 30× potency, Ignatia Amara in 30× potency, Pulsatilla in 30× potency and Cantharis in 30× potency; Mineral oil 12% by weight; Avena Sativa 80% by weight; Calcium Silicate 7.37% by weight; and Ethoxylated Aliphatic Alcohol 0.63% by weight.

2. A composition as in claim 1 where the said composition is administered into the vaginal canal by bath.

3. A composition as in claim 1 for the treatment of vaginal dryness.

4. A composition as in claim 1 for the treatment of burning sensation around the vagina.

5. A composition as in claim 1 for the treatment of vaginal irritation.

6. A composition as in claim 1 for the treatment of redness around the vagina.

7. A composition as in claim 1 for the treatment of vaginal discomfort.

8. A composition as in claim 1 for the treatment of vaginal soreness.

9. A composition as in claim 1 for the treatment of vaginal redness.

10. A method for symptomatic treatment of vaginitis in subjects in nee thereof by the application of a composition comprising; Apis Mellifica in 30× potency, Borax in 30× potency, Hydrastis Canadensis in 30× potency, Kali Bichromicum in 30× potency, Helonias Dioica in 30× potency, Lycopodium Clavatum in 30× potency, Sepia in 30× potency, Agaricus Muscarius in 30× potency, Anagallis Arvensis in 30× potency, Dolichos Pruriens in 30× potency, Muriaticum Acidum in 30× potency, Oleander in 30× potency, Arsenicum Album in 30× potency, Kali Muriaticum in 30× potency, Berberis Vulgaris in 30× potency, Urtica Urens in 30× potency, Ignatia Amara in 30× potency, Pulsatilla in 30× potency and Cantharis in 30× potency; Mineral oil 12% by weight; Avena Sativa 80% by weight; Calcium Silicate 7.37% by weight; and Ethoxylated Aliphatic Alcohol 0.63% by weight.

11. A method as claimed in claim 10 for the removing the dead tissue from the vagina where said composition is applied to the vaginal area.

12. A method as claimed in claim 10 for the cleansing the vagina and vaginal area during inflammation where said composition is applied to the vaginal area.

13. A method as claimed in claim 10 for the cleansing the vagina and vaginal area during infections where said composition is applied to the vaginal area.

14. A method as claimed in claim 10 for the symptomatic treatment of vaginitis where said composition is applied to the vaginal area.

15. A method as claimed in claim 10 for the symptomatic treatment of sexually transmitted diseases where said composition is applied to the vaginal area.

16. A method as claimed in claim 10 for the symptomatic treatment of vaginitis where the said composition is administered into the vaginal canal by bath.

* * * * *